United States Patent [19]

Papantonakos

[11] Patent Number: 4,717,381
[45] Date of Patent: Jan. 5, 1988

[54] HYDRODYNAMICALLY PROPELLED CATHETER

[75] Inventor: Apostolos C. Papantonakos, Athens, Greece

[73] Assignee: Kos Medical Technologies, Ltd., Tampa, Fla.

[21] Appl. No.: 862,677

[22] Filed: May 13, 1986

[30] Foreign Application Priority Data

May 13, 1985 [GR] Greece ......................... 1148

[51] Int. Cl.⁴ .......................................... A61M 37/00
[52] U.S. Cl. ........................................ 604/95; 604/96; 128/672; 128/419 P; 128/786
[58] Field of Search ..................... 604/95, 96; 128/672, 128/783-786, 419 P

[56] References Cited

U.S. PATENT DOCUMENTS

| | | | |
|---|---|---|---|
| 1,115,908 | 11/1914 | Dees | 604/95 |
| 2,356,659 | 8/1944 | Aguiar | 604/95 |
| 2,393,728 | 1/1946 | Aguiar | 604/95 |
| 3,279,460 | 10/1966 | Sheldon | 604/95 |
| 3,937,225 | 2/1976 | Schramm | 128/419 P |
| 4,403,985 | 9/1983 | Boretos | 604/95 |
| 4,475,902 | 10/1984 | Schubert | 604/256 |
| 4,519,403 | 5/1985 | Dickhudt | 128/786 |

FOREIGN PATENT DOCUMENTS

2267800 11/1975 France ........................... 604/95

Primary Examiner—Stephen C. Pellegrino
Assistant Examiner—Gene B. Kartchner
Attorney, Agent, or Firm—Pettis & McDonald

[57] ABSTRACT

A hydrodynamically propelled catheter primarily intended for use in the placement of temporary pacemakers into the right ventricle of a patient. The cephalic end of the catheter is constructed to define a plurality of nozzle orifices for the expulsion of a pressurized fluid so that the catheter will be propelled through the patient's vascular system, past the tricuspid valve, and into the right ventricle. Standard electrodes are provided, and the cathether may further include a balloon segment disposed rearwardly of the cephalic end.

13 Claims, 14 Drawing Figures

HYDRODYNAMICALLY PROPELLED CATHETER

BACKGROUND OF THE INVENTION

1. Field of the Invention

The present invention relates to a hydrodynamically propelled catheter for the placement of temporary pacemaker leads into the right ventricle of a patient.

2. Description of the Prior Art

Modern cardiology would not have been nearly so successful if cardiac catheterization had not been realized, initially, for diagnostic and, subsequently, for therapeutic purposes. Cardiac catheterizations are conducted quite routinely today, with the results of such procedures normally being expressed in emperical measurements, and these measurements are used in both diagnosis and treatment.

A primary field of cardiac catheterization treatment is right ventricle pacing, for the insertion of temporary pacemaker leads into the right ventricle, by using a catheter to insert those leads. According to today's relatively standard catheterization procedures, the cephalic end of the catheter is inserted either through the femoral vein or through the subclavical vein into the patient's right atrium. The relatively delicate portion of the insertion procedure is then to pass the catheter through the tricuspid valve and into the patient's right ventricle. A primary purpose of the investigation and study resulting in the development of the hydrodynamically propelled catheter of this invention was to simplify entry into the right ventricle for the purpose of minimizing the operation time and, thus, reducing additional stress to the already "hemodynamically" damaged patient. As is set forth in greater detail below, it has been determined that the use of a hydrodynamically propelled catheter in accord with this invention efficiently and safely accomplishes those results.

It is, of course, understood that numerous forms of cardiac catheters are well known in the prior art. Furthermore, a search of pertinent prior art literature has revealed the existence of devices constructed to utilize hydrodynamic forces during the catheterization procedure. A construction for one such catheter is disclosed in U.S. Pat. No. 4,403,985 issued to Boretos and titled Jet Controlled Catheter. According to the disclosure of that patent, the leading end of a catheter tube may be controlled, directionally, by pressurized control fluid issued from selected control ports formed through the tube substantially adjacent its forward end. The catheter of this patent includes a pleated section just rearward of the control ports so that the leading end may bend or turn. Another prior art device is disclosed in U.S. Pat. No. 4,475,902 to Schubert, and titled Device for Introducing Medical Instruments into a Body. According to the disclosure of this patent, at least one nozzle, aimed rearwardly with respect to the tip of the device, is provided. Pressurized fluid may escape from this nozzle to exert a force on the device tip to advance it into the body, thereby transporting an instrument coupled to the nozzle tip through the body. Yet another catheter including a plurality of orifices formed just behind its leading end for the discharge of a fluid to impart a thrusting force to the catheter is disclosed in French Pat. No. 74 13271.

However, without in any way questioning the utility of the prior art devices as disclosed and explained in these patents, it is not only significant but somewhat surprising to note the virtual absence of any technical literature discussing or presenting the desirability of utilizing such prior art catheters for the purpose of placing temporary pacemaker leads into a patient's right ventricle. In fact, the current state of the art seems to utilize, primarily, normal blood flow and manual manipulation as observed by x-rays for temporary pacemaker lead insertion. Even though modern medical technology recognizes the necessity of a relatively swift, nontraumatic passage of the catheter through the tricuspid valve, there appears to be no teaching in the prior patent literature of a cather construction which will accomplish these results by the use of hydrodynamic forces. It is therefore clear that a great need in the art remains for a hydrodynamically propelled catheter construction specifically and uniquely designed for temporary pacemaker lead insertion into the right ventricle of a patient.

SUMMARY OF THE INVENTION

Briefly stated, the catheter of this invention is in the nature of a heart catheter for inserting temporary pacemaker leads into the right ventricle of a patient. The cephalic end of the catheter is constructed to include a plurality of rearwardly facing orifices, or ports. These ports are in fluid communication with a fluid lumen through which a pressurized fluid may be passed for expulsion through the ports. Because the ports are rearwardly oriented with respect to the cephalic end of the catheter, a propelling force, or thrust, will be imparted to the catheter upon passing the fluid therethrough. Valve means are provided for regulating the flow of fluid through the fluid lumen and out of the ports.

The hydrodynamically propelled catheter further includes electrodes which are electrically connected to a source of pacing electricity, whereby the ultimate temporary pacemaker function may be accomplished. In the preferred embodiment, the cephalic end of the catheter, through which the fluid ports are formed, defines a first electrode, while a second electrode is spaced rearwardly therefrom. Furthermore, the hydrodynamically propelled catheter of this invention may comprise a balloon segment disposed intermediate the electrodes. A valved gas lumen communicates with the balloon segment, whereby the balloon segment may be selectively inflated and deflated. It is to be understood that utilization of the balloon segment in the construction of the hydrodynamically propelled catheter of this invention, while desirable, is not to be imposed as a structural limitation on the scope of the invention. Inasmuch as the gas lumen is valved, it is not required that the balloon segment be inflated pursuant to the scope of the present invention. Accordingly, the hydrodynamically propelled catheter of this invention could be constructed without any balloon segment at all.

The invention accordingly comprises the features of construction, combination of elements, and arrangement of parts which will be exemplified in the constructions hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying graphs, drawings and tables, in which.

TABLE 1 is a summary of the comparative data presented in the graphs of FIGS. 1–6.

Similar reference characters refer to similar parts through the several views of the drawings.

DETAILED DESCRIPTION

While specific embodiments for the hydrodynamically propelled catheter of this invention will be discussed below, certain general statements concerning catheter construction are relatively standard among all embodiments. It is, of course, to be understood that these "standard" characteristics are presented for illustrative purposes only in order to enable one skilled in the art to practice the invention described and claimed herein. The scope of the invention is not to be limited by these general characteristics of materials and sizes. It is also to be understood that the hydrodynamically propelled catheter of this invention would be used in combination with other equipment and procedures normally utilized for heart catheterization for the purpose of inserting temporary pacemaker leads.

Average length of the catheter falls within the range of from about 75 cm to about 120 cm. The preferred external diameter of the catheter is about 0.23 cm. The surface area of the cephalic tip is about 0.04152 cm$^2$. Each embodiment of the catheter has at least two lumens. A fluid lumen is generally disposed along the axis of the catheter, and a second lumen is provided for inflating the cather's balloon. Balloon inflation may be accomplished by air or by carbon dioxide. The balloon is positioned substantially adjacent the cephalic end of the catheter, between the cather's two electrodes. When inflated, the balloon's diameter is about 1 cm, and it has a capacity of about 1.3 cm$^3$.

Preferably, the electrical system of the pacing catheter is constituted by two poles, or electrodes, formed as rings around the catheter. The first electrode is the cephalic end, and the second electrode is spaced apart from the first electrode. When the catheter is constructed to include a balloon, the balloon is disposed between the two electrodes. Of course, appropriate electrical conduits are connected to each electrode whereby a pacing current may be applied to the patient.

At the external end of the catheter there are two orifices, one of which communicates with each of the respective fluid and air lumens. As indicated above, either air or carbon dioxide may be injected in to the air lumen for inflating the balloon, and the air lumen is valved. The fluid lumen is utilized for injecting a definite amount of normal saline solution (volume per time) and is also valved. As will be explained in greater detail, it is the expulsion of normal saline from ports formed substantially adjacent the cephalic tip of the catheter of this invention which provide a hydrodynamic force to assist in its proper placement within the patient's right ventricle.

At least a pair of fluid ports are formed at the cephalic tip of the catheter in symmetrical relation to each other, and these ports are in fluid communication with the fluid lumen. The ports are angled rearwardly, preferably at an angle of about 30° with respect to the axis of the catheter, so that fluid will be expelled rearwardly therefrom, imparting a forward thrust to the catheter's cephalic tip. Though not strictly limited thereto, a preferred diamter for the fluid ports is about 0.05 cm, resulting in a port area of about 0.0019 cm$^2$.

Pursuant to known procedures and technique, the catheter body is preferably formed from a radiopaque polyvinylchloride having marks along its length every 10 cm. The electrode rings are preferrably formed from stainless steel.

Initial insertion procedures are substantially identical for all embodiments of the hydrodynamically propelled catheter of this invention. First, the fluid lumen is filled with normal saline and its valve is closed before initial insertion. Known techniques are utilized for inserting the catheter into the patient's venous systems into the right atrium. At this point, the balloon segment is preferably inflated and normal saline solution is injected through the fluid lumen to be expelled from the fluid ports. This creates a forward force on the catheter cephalic tip significantly enhancing both the speed and efficiency of passage through the tricuspid valve into the patient's right ventricle. As is shown in detail comparative figures below, placement of the temporary pacemaker leads utilizing a hydrodynamically propelled catheter in accord with this invention is much mor efficient than placement without such hydrodynamic assistance.

Figures 7, 7A:
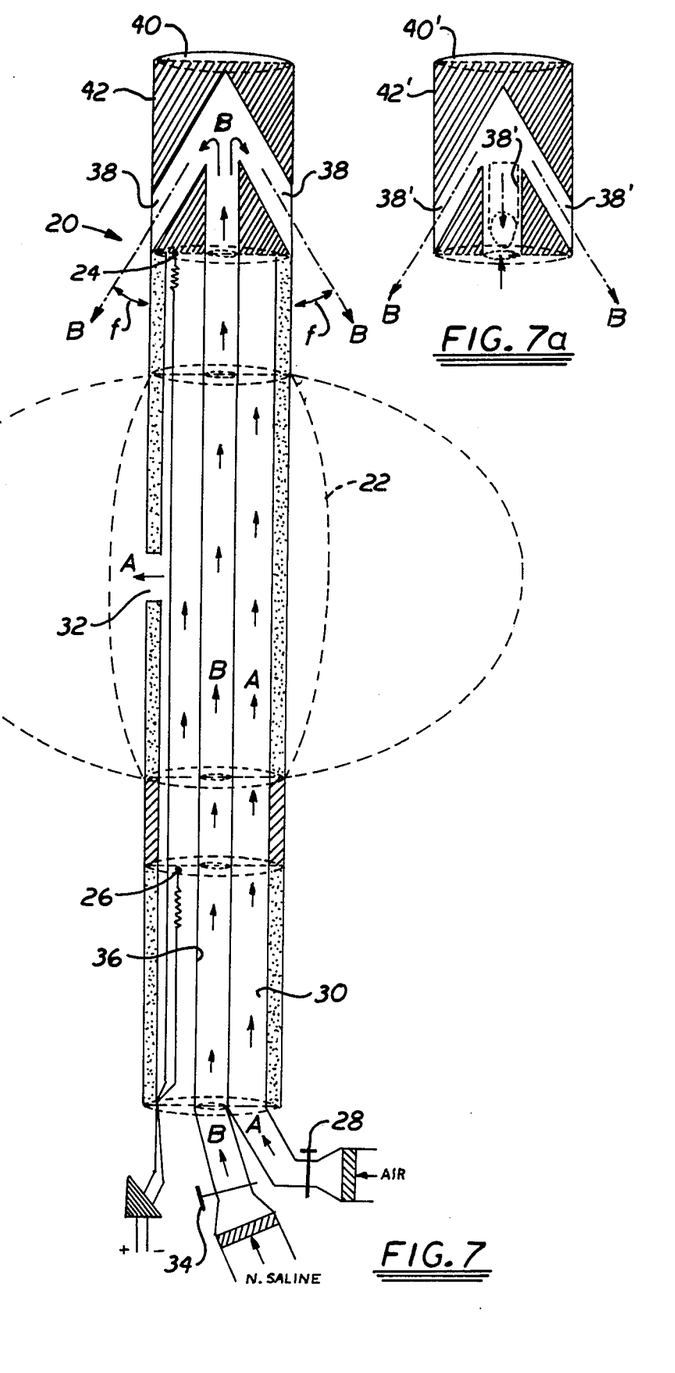
FIG. 7 illustrates a first embodiment for the hydrodynamically propelled catheter of this invention having two fluid ports.
FIG. 7a illustrates the cephalic tip of the catheter of FIG. 7 modified to include three fluid ports.

Referring now to the view of FIG. 7, a first embodiment 20 of the hydrodynamically propelled catheter is depicted. A balloon segment 22 is shown in dotted lines intermediate the length of catheter 20 between first electrode contact 24 and second electrode contact 26. Balloon segment 22 may be inflated by permitting air to pass valve 28 into air lumen 30 and out air orifice 32. Air flow is indicated by directional arrows A.

Hydrodynamic fluid (normal saline solution) is admitted into catheter 20 past fluid valve 34, into fluid lumen 36, and fluid is expelled through fluid ports 38. Fluid flow is indicated by directional arrows B. As clearly seen in the view of FIG. 7, fluid ports 38 define an angle f of about 30° and are rearwardly facing with respect to distal end 40 of the catheter's cephalic tip 42. Distal end 40 is closed in the embodiment 20 shown in the view of FIG. 7.

FIG. 7a shows a cephalic tip 42' substantially identical to that of FIG. 7. The structural difference between the tip of FIG. 7a and that of FIG. 7 is the formation of three fluid ports 38', equally spaced in tip 42' and each communicating with fluid lumen 36. It has been determined that the existence and operation of the three-port embodiment of FIG. 7a results in better balance and control of the catheter as it moves past the tricuspid valve.

Figures 8, 8A:
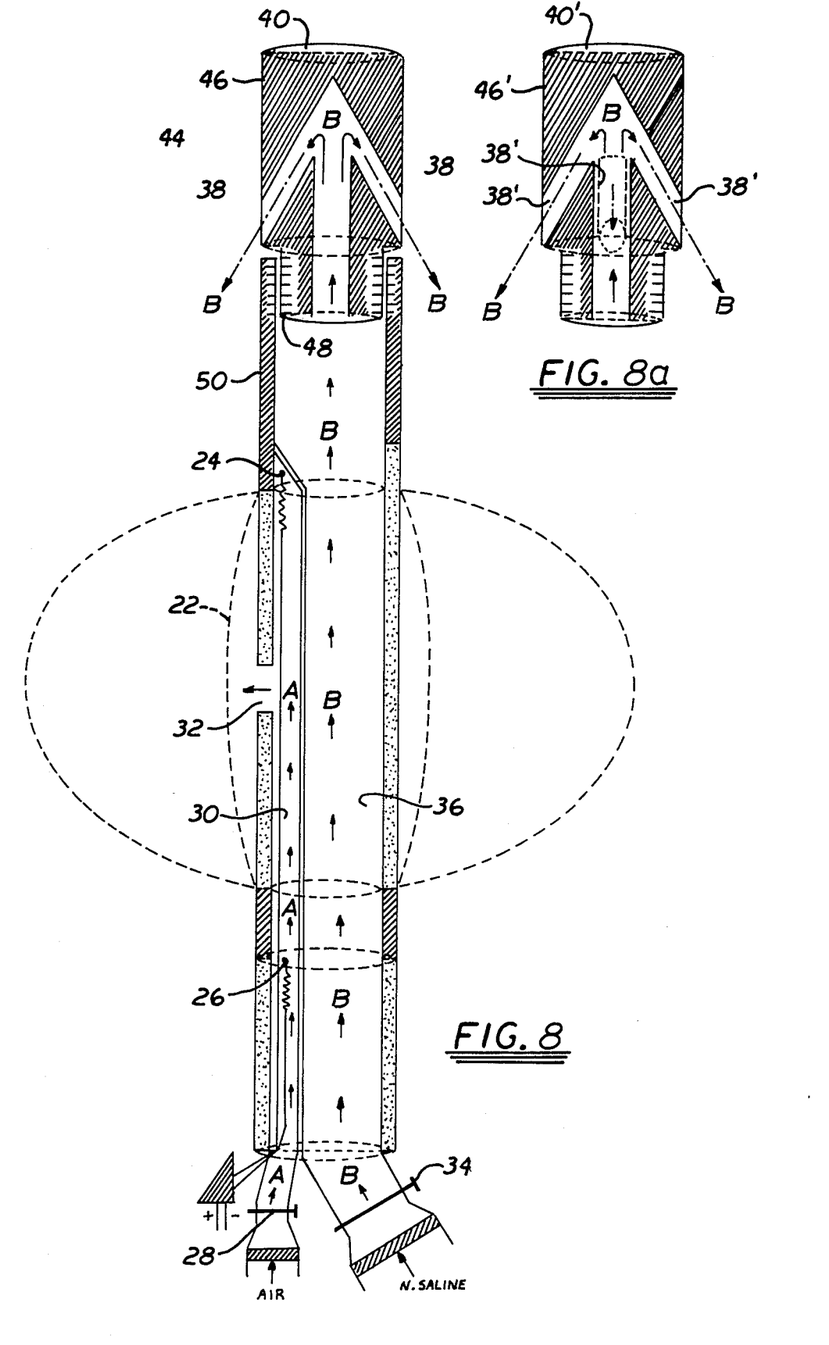
FIG. 8 illustrates a hydrodynamically propelled catheter similar to that of FIG. 7 wherein the cephalic end is removable.
FIG. 8a illustrates the cephalic tip of the catheter of FIG. 8 modified to include three fluid ports.

FIG. 8 shows a second embodiment 44 for the hydrodynamically propelled catheter of this invention. Upon comparing catheter 44 with catheter 20, it can be seen that a primary structural difference is the fact that cephalic tip 46 of catheter 44 is removably attached as by threads 48 to catheter tube 50. In this embodiment 44, the fluid lumen 36 is enlarged, and the air lumen 30 is narrowed, but their operation and use are virtually identical to that described with regard to drawing FIG. 7.

In FIG. 8a, an alternate construction for removable tip 46' is shown and comprises three fluid ports 38' in a fashion similar to that of FIG. 7a.

Figures 9, 9A:
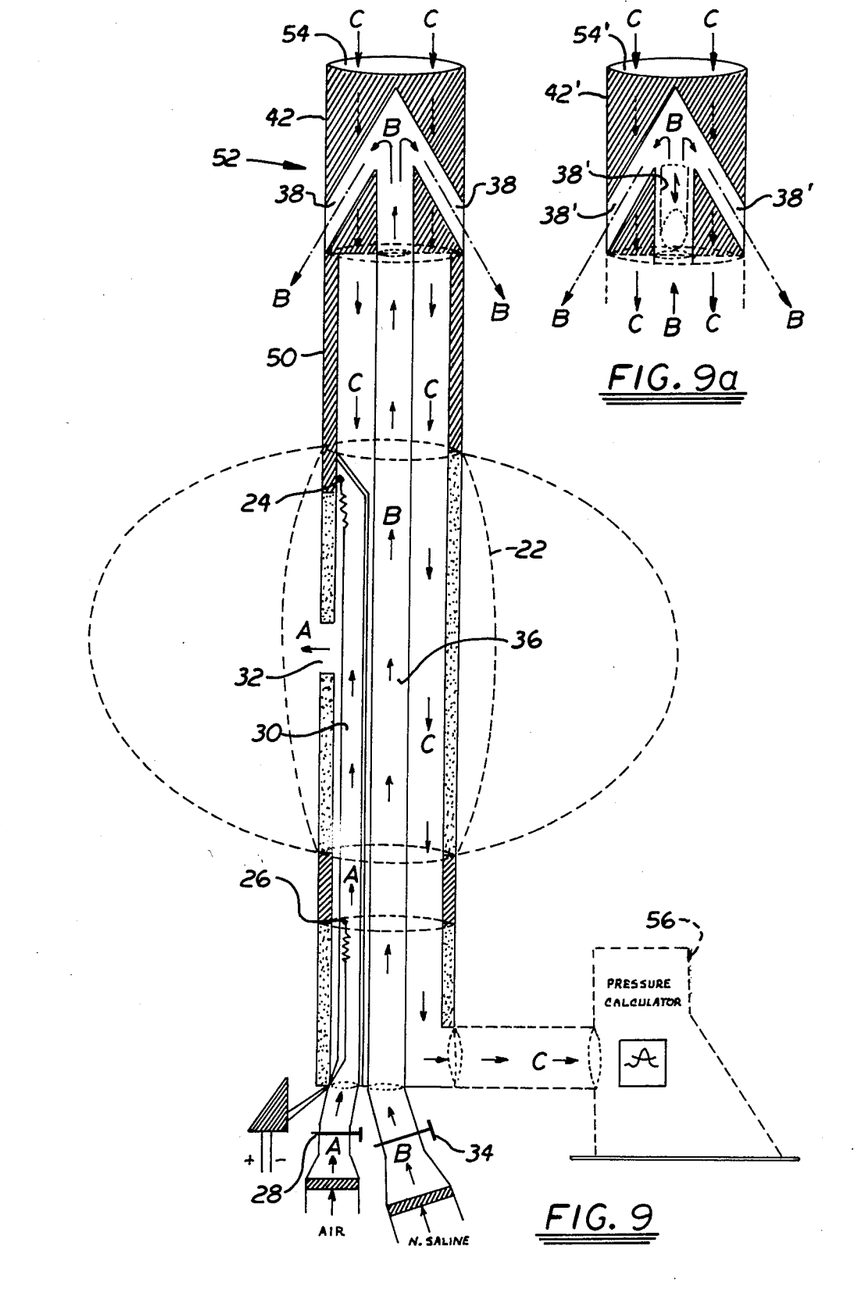
FIG. 9 illustrates an alternate embodiment of the hydrodynamically propelled catheter wherein the distal end of the cephalic tip is open to permit measurement of blood pressure.
FIG. 9a illustrates the cephalic tip of the catheter of FIG. 9 modified to include three fluid ports.

The view of FIG. 9 represents a third embodiment 52 of the hydrodynamically propelled catheter. The cephalic tip 42 is substantially identical to that of FIG. 7 with one significant modification. Distal end 54 of third embodiment 52 is open to permit the passage of the patient's blood therethrough for pressure monitoring as by the external pressure calculator schematically indicated at 56. Blood flow through catheter 52 is indicated by directional arrows C. Other structural details of this third embodiment 52 correspond to those of catheter 20 shown in FIG. 7. As with FIGS. 7a and 8a, drawing FIG. 9a represents a cephalic tip 42' including three fluid ports 38'. In other respects, cephalic tip 42' of FIG. 9a corresponds to tip 42 of FIG. 9.

Figure 10:
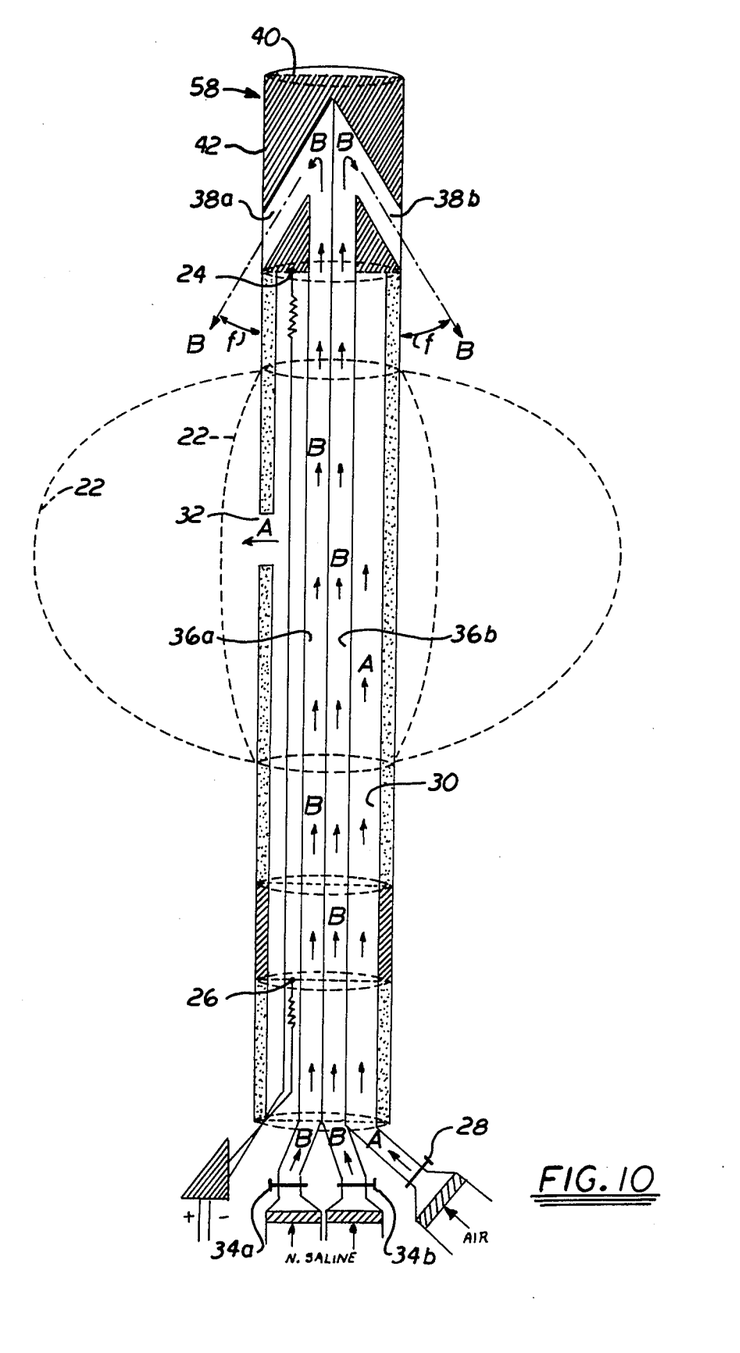
FIG. 10 illustrates yet another embodiment of the hydrodynamically propelled catheter of this invention wherein a separate fluid lumen communicates with each fluid port to permit enhanced lateral mobility of the catheter.

Yet a fourth embodiment 58 for the hydrodynamically propelled catheter of this invention is shown in drawing FIG. 10. While the construction of catheter 58 is almost identical to catheter 20 of FIG. 7, one significant structural distinction is the provision of two fluid lumens 36a and 36b. Furthermore, fluid lumen 36a communicates with fluid port 38a, and fluid lumen 36b communicates with fluid port 38b. Since each of the fluid lumens further includes its individual fluid valve 34a and 34b, normal saline solution may be passed through either one or both of the fluid ports 38a and 38b. Construction of catheter 58 to define separate, distinct fluid passages as shown in FIG. 10 permits greater lateral mobility of cephalic tip 42. It is, of course, to be understood that the number of fluid ports could be increased with a corresponding increase of fluid lumens and associated valves.

Having thus set forth preferred embodiments for constructions of a hydrodynamically propelled catheter, attention is now invited to the following theoretical calculations demonstrating the enhanced utility and safety of such a catheter for the placement of temporary pacemakers in a patient's right ventricle. For purposes of these theoretical considerations, blood flow velocity at the diastolic period of the cardiac cycle must be considered for it is at that period when the cephalic tip of the pacing catheter will be at the lower point of the patient's right atrium, immediately before the tricuspid valve orifice, "waiting" for that valve to open so that the pacemaker leads may be inserted into the right ventricle.

If we suppose that about 5.000 cm$^3$ of blood are passed through an orifice, just before the tricuspid valve orifice at every minute, at the diastolic phase (about 0.38 sec) having a cardiac frequency about 90/min., the diastolic filing period will be:

$$0.38 \times 90 = 34 \text{ sec/min.}$$

So, the diastolic blood's flow will be about 147 cm$^3$/sec. Diastolic blood's flow period is subdivided in three periods and starts with the tricuspid valve opening (in right circulation). Blood will start flowing from the right atrium to the right ventricle. In this "rapid filling" phase, blood's flow is influenced by the pressure gradient, between the right atrium and the right ventricle (approximately from V wave to Y wave of the right atrium's pressure curve). This period will be about 0.06–0.09 sec. and is approximately estimated by hemodynamic curves and Echocardiograms of the tricuspid valve.

The second period of diastolic blood's flow, immediately starts and finishes in a wave. This period is called "slow diastolic filling period." At this phase, there is a minimum blood flow because of a small gradient existence, when the cusps of the tricuspid valve are slightly opened. This time period is about 0.20–0.22 sec.

The last period of diastolic phase, begins from the start of atrium contraction, in which the blood's flow makes the cusps of tricuspid valve open. This period terminates at the moment of tricuspid valve closure, and the duration of the period, is approximately 0.10 sec. The third phase (right atrium contraction) participates in right ventricle filling at about 20 percent (20%), that is to say about 29 cm$^3$/sec of blood.

If one would suppose that the blood volume which is passed through at the second diastolic phase is small, (because of small pressure gradient) when the cusps of tricuspid valve are slightly opened, then the greatest volume will be passed at the V-Y phase (about 100 cm$^3$/sec.).

If one would suppose that there is an "hypothetical" lower right atrium orifice, just before the tricuspid valve and its diameter is about 4 cm, the corresponding surface orifices (if is supposed that right atrium looks like a cylinder) will be:

$$S = \pi \times R^2 = 12.56 \text{ cm}^2.$$

Dividing the blood's volume which is passed through this orifice, at V-Y phase, we will have an approximate blood flow velocity of 7.96 cm/sec.

Now, one must consider the influence of these blood flow parameters on the cephalic tip of the pacing catheter, which is waiting at the same lower right atrium's level, just before the tricuspid valve orifice. One must also estimate the total surface defined by the initial (cephalic) 5 cm of the catheter, as well as the sectional surface of the inflated balloon. The inflated balloon has a 1 cm diameter and contains about 1 cm$^3$ of air. The balloon's sectional surface will be about 0.78 cm$^2$. The sectional surface of the first 5 cm of the catheter will be about 1.15 cm². The coefficient of resistance of the inflated balloon is 0.25 and the coefficient of resistance of the catheter is about 0.90. After that, we shall study the "total" resistance which is created, because of blood flow, using the next type:

$$T_B = k \times p \times S \times U_B^2 , \quad (1)$$

where,
T$_B$=Total blood's resistance (dynes)
k=Coefficient resistance, (depends on the form of the object).
p=Density of blood (here we use not 1.05-106 but 1.0).
S=The sectional surface (cm²).
U$_B$=Blood velocity (cm/sec.).

$$\text{But } T_B = T_{B1} + T_{B2},$$

where,
T$_{B1}$=Blood's resistance on inflated balloon.
T$_{B2}$=Blood's resistance on the initial segment of the catheter. (cylinder 5 cm).
So, that at (V-Y phase:)
T$_{B1}$=0.25×0.78×7.96²=12.35 (dynes).
T$_{B2}$=0.90×1.15×7.96²=65.57 (dynes).
and T$_B$=T$_{B1}$+T$_{B2}$=77.92 (dynes).
At phase (a).
T$_{B1}$=0.25×0.18×2.3²=1.03 (dynes).
T$_{B2}$=0.90×1.15×2.3²=5.47 (dynes).
T$_B$=T$_{B1}$+T$_{B2}$=6.5 (dynes).
Thus, at the V-Y phase, the catheter cephalic tip receives about 77.92 dynes (the maximum) force forwards, and at (a) phase, about 6.5 dynes.
Now we consider the corresponding acceleration of the catheter cephalic tip because of the diastolic blood flow. For this purpose we determine the mass (M), of the initially 10 cm of the catheter. The weight of this is about 0.25 g.
When the balloon segment is inflated, the cephalic tip is lighter and the balloon helps it to be placed in a more "central" position, where the blood's velocity is higher. So, using the well known formula:

$$U = g \times t \quad (2) \quad \text{and} \quad S = \tfrac{1}{2} g \times t^2 \quad (3),$$

we estimate the acceleration and the distance traveled of the cephalic tip at phases (V-Y) and (a).
At phase V-Y:

$$gp = \frac{T_B}{M} \quad (4)$$

$$gp = \frac{77.92}{0.25} = 311.68 / \frac{cm}{sec^2}$$

(P) indicates "passive," helped only by blood flow.
If t=0.06 (sec), U$_p$=3.11.68×0.06=18.70 (cm/sec) and S$_p$=0.56 (cm).
If t=0.09 (sec), U$_p$=28.05 (cm/sec) and S$_p$=1.26 (cm).

At phase (a):
If t=0.10 (sec), gp=6.5/0.25=26 (cm/sec²).
U$_p$=2.6 (cm/sec) and S$_p$=0.13 (cm).
The intervals of time which have been determined are only those at which the cephalic tip can be passed through the tricuspid valve.
Now, we will consider the catheter's "moving" parameters, which arise (in addition to blood flow) when we also operate the "hydrodynamic system."
The cephalic tip of the catheter is placed at the right atrium before the tricuspid valve, just after filling the water lumen with normal saline and heparine (for avoidance of lumen orifices thrombosis and pulmonary air embolization). At this place, there is a forward force by the diastolic blood's flow and, when we inject normal saline through the water lumen we add another forward force F, on the cephalic tip.
This forward force depends on the velocity (U$_1$ and sectional surface of the saline injector piston (S$_1$). If these are (n) ports on the cephalic tip, the velocity of normal saline flow which comes out will be:

$$U_2 = \frac{S_1 \times U_1}{n \times S_2} \quad (5)$$

where,
S$_2$=surface of each water lumen.
The relative (with catheter) velocity of normal saline flow which comes out will be:

$$U = n \times U_2 \times \cos \times f \quad (6)$$

where, cosf=the cosine of angle f, that is to say, the angle which is made between each fluid port orifice and the longitudinal axis of the catheter.
The formula:

$$F = -\frac{dm}{dt} \times U_2 \quad (7)$$

gives the forward force, because of the existence of normal saline flow through the fluid ports.
The formula:

$$M = p \times V \quad (8)$$

where M=mass (of normal saline), p=the density of normal saline and V=the volume of this, we derive the following formula:

$$F = -\frac{P(U_1 \times S_1)^2}{S_2} \times \cos f \, (9) \, (F = \text{in dynes}).$$

Here, it is observed that the weight of the initial 10 centimeters of the catheter, without normal saline, is about 0.25 gr. The weight with the water lumen filled by normal saline (hydrodynamic system operation) will be, as it has been estimated, about 0.66 gr. After this, we also estimate the acceleration, the velocity and the distance travelled of the cephalic tip of the catheter with hydrodynamic assistance.
We apply the following formulas:

$$g_T = \frac{P(U_1 \times S_1)^2 \times \cos f}{S_2 \times M} \tag{10}$$

$g_T$ = total acceleration (in cm/sec$^2$) (acceleration which has resulted from hydrodynamic system operation, in addition to the diastolic blood flow).

$$U_T = \frac{P(U_1 \times S_1)^2 \times \cos f}{S_2 \times M} \quad (U_T = \text{total velocity}) \tag{11}$$

$$S_T = \frac{P(U_1 \times S_1)^2 \times \cos f \times t^2}{2 \times S_2 \times M} \quad (S_T = \text{total distance travelled}) \tag{12}$$

A catheter, having a sectional surface of about 0.04152 cm$^2$, three angled water ports, each being about 0.0019 cm$^2$ in surface and an angle f=30° gives the results which are shown on Table 1. On Table 1 are described the "moving" parameters of the cephalic tip of the catheter which are dependent on the injected normal saline volumes and the blood flow. Table 1 compares these parameters with the parameters of "passively" moving catheters (without hydrodynamic system operation).

If the coefficient of friction of the polyvinylchloride catheter is about 2, the coefficient of friction is given by the following equation:

$$F = F/W \tag{13}$$

where F=the minimum attractive force which is necessary to obtain the least catheter's moving which is in contact with a non lubricated metal surface, and having the weight of catheter (the first ten cm)=0.66, we find out the minimum pulling (attractive) force, which is necessary to move this catheter, as follows:

$$F = 2 \times 0.66 = 1.32 \text{ gr, or } 1294.92 \text{ dynes}$$

That is to say that we need this minimum force in order to obtain the least moving but it is estimated "in vitro" conditions and having friction forces on a metal surface.

When the catheter will be moved "in vivo" conditions, through a liquid (as blood), we need a diminished force to move it slightly.

Another advantage of a "hydrodynamic" catheter is when we use it in pathological hemodynamic conditions, where exists a poorest help from only the diastolic blood's flow.

Figure 1:
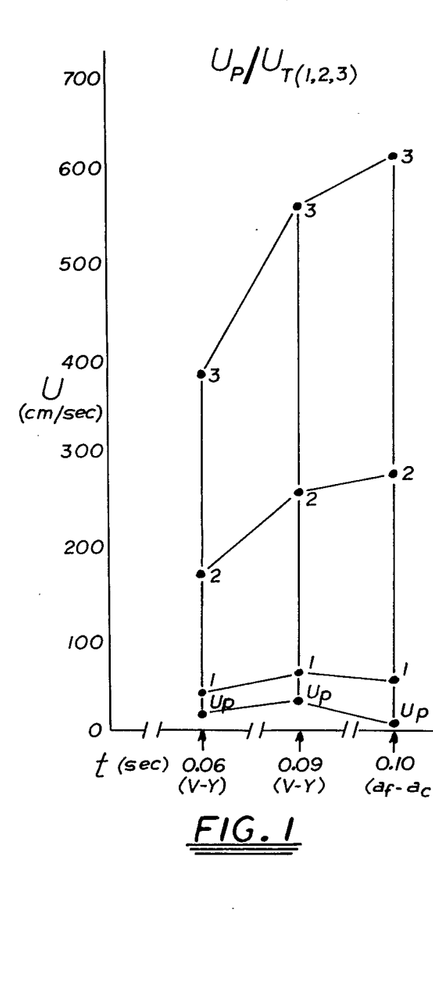
FIG. 1 is a graphic comparison of catheter velocity without hydronamic assistance and with hydrodynamic assistance.
Figure 2:
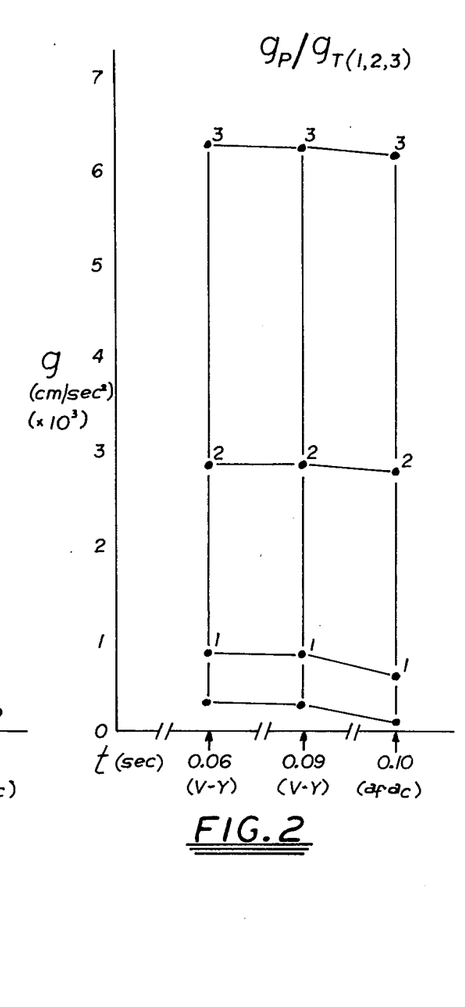
FIG. 2 is a graphic comparision of catheter acceleration without hydrodynamic assistance and with hydrodynamic assistance.
Figure 3:
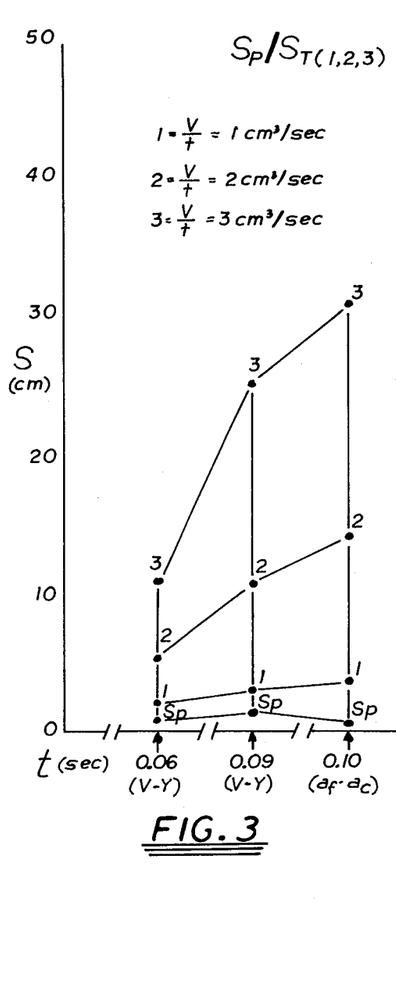
FIG. 3 is a graphic comparison of catheter distance travelled without hydrodynamic assistance and with hydrodynamic assistance.

At FIGS. 1, 2 and 3, one sees graphically, and can compare, the moving parameters of velocity acceleration and the distance travelled of the cephalic tip of catheter, which are dependent on the injected (volume/time) normal saline flows, passively and in addition to the hydrodynamic system operation.

Figure 4:
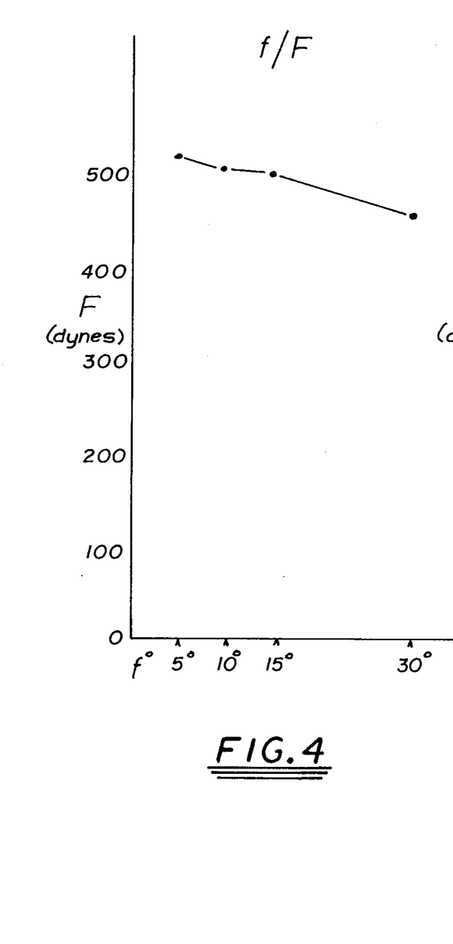
FIG. 4 is a graphic representation of the effect of the angle of the exit ports with respect to the axis of the catheter on the forward force generated.

FIG. 4 graphically expresses the influence of angle f on the forward force. For example, if one decreases this angle from 30° to 15°, an increase of the forward force (F) of about 12% will result. The increase of this force will be about 16%, if one decreases this angle from 30° to 5°.

Figures 5, 6:
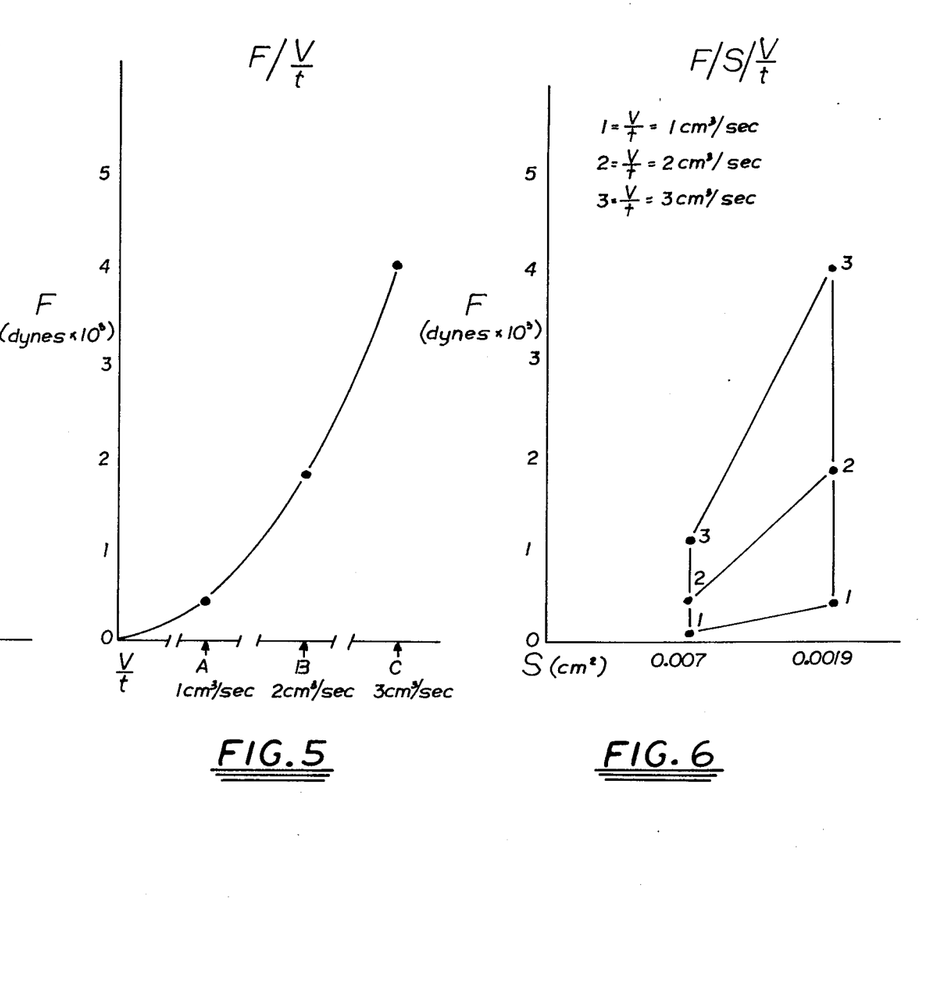
FIG. 5 is a graphic representation of the effect of volume of fluid per time expelled on the forward force generated.
FIG. 6 is a graphic representation of the effect of orifice/port area on the forward force generated.

FIG. 5 expresses the curve of forward force, which is dependent on the volum per time which has been injected.

FIG. 6, shows the effect of the area of the fluid port on forward force alterations. For example, if the area of each port is changed from 0.07 cm$^2$ to 0.0019 cm$^2$ (is decreased in 1:3), there will be a 100% increase of forward attractive force on the catheter's cephalic tip.

It will thus be seen that the objects set forth above, among those made apparent from the preceding description, are efficiently attained, and since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. A hydrodynamically propelled catheter of the type primarily used for insertion of temporary pacemaker into the right ventricle of a patient's heart, said catheter comprising; an elongated flexible catheter tube for insertion through the patient's blood vessels into the right ventricle, said catheter tube having a cephalic end and a rearward end; said cephalic end including a plurality of rearwardly facing ports substantially equally spaced around the perimeter thereof, eaach of said ports including an axis which defines an angle with the axis of said catheter tube of from about 5° to about 30°; said catheter tube further having at least one fluid lumen disposed longitudinally inside said tube, a distal end of said fluid lumen being in fluid-communicating relation to at least one of said ports and a rearward end of said fluid lumen exiting said catheter tube rearward end, said fluid lumen rearward end being operatively connected to a fluid source whereby fluid may pass from the source through said fluid lumen and be expelled through at least said one port to impart a forward thrust to said cephalic end; said catheter further comprising spaced apart first and second pacing electrodes, said first electrode being disposed substantially adjacent said cephalic end and said second electrode being disposed rearwardly of said cephalic end, both said first and second electrodes being positioned for electrical contact with the patient and being operatively connected to a source of electricity whereby an electrical stimulus may be applied to the patient's heart.

2. A hydrodynamically propelled catheter as in claim 1 wherein said distal end of said fluid lumen is in fluid-communicating relation to each of said ports.

3. A hydrodynamically propelled catheter as in claim 1 wherein said angle is about 30°.

4. A hydrodynamically propelled catheter as in claim 1 wherein said angle is about 15°.

5. A hydrodynamically propelled catheter as in claim 1 wherein said angle is about 5°.

6. A hydrodynamically propelled catheter as in claim 1 wherein said catheter further comprises a balloon segment disposed in surrounding relation to said catheter tube between said first and said second electrode; said catheter tube further including an air lumen disposed longitudinally inside said tube, a distal end of said air lumen being in gas-communicating relation to said balloon segment and a rearward end of said air lumen exiting said catheter tube rearward end, said air lumen rearward end being operatively connected to a gas source whereby said balloon segment may be inflated.

7. A hydrodynamically propelled catheter as in claim 6 further comprising valve means operatively disposed between said air lumen rearward end and the gas source whereby inflation and deflation of said balloon segment may be controlled.

8. A hydrodynamically propelled catheter as in claim 1 further comprising a fluid valve operatively disposed between said fluid lumen rearward end and the fluid source whereby the volume and rate of fluid flow may be controlled.

9. A hydrodynamically propelled catheter as in claim 1 comprising a plurality of said fluid lumens, said distal end of each of said lumens being in fluid-communicating relation to a corresponding one of said ports, and said rearward end of each of said lumens being operatively connected to a fluid source.

10. A hydrodynamically propelled catheter as in claim 9 further comprising a plurality of fluid valves, one of each of said plurality being operatively disposed between each of said fluid lumen rearward ends and the fluid source whereby the volume and rate of fluid flow through each of said ports may be controlled.

11. A hydrodynamically propelled catheter as in claim 1 further comprising an open distal end of said cephalic end in fluid-communicating relation to the interior of said catheter tube whereby the patient's blood may enter said tube, said rearward end of said tube being in fluid-communicating relation to a blood pressure calculator means, whereby the patient's blood pressure may be monitored.

12. A hydrodynamically propelled catheter as in claim 1 wherein said cephalic end is removably attachable to said catheter tube.

13. A hydrodynamically propelled catheter as in claim 12 wherein said cephalic end is screwed onto said catheter tube.

* * * * *